(12) United States Patent
Liou et al.

(10) Patent No.: US 10,357,524 B2
(45) Date of Patent: Jul. 23, 2019

(54) METHOD FOR TREATING HEPATITIS B

(71) Applicant: HAN SHENG PHARMTECH, INC., Pingtung County (TW)

(72) Inventors: Shorong-Shii Liou, Pingtung County (TW); I-Min Liu, Pingtung County (TW); Hung-Tsung Wu, Pingtung County (TW)

(73) Assignee: HAN SHENG PHARMTECH, INC., Pingtung County (TW)

( * ) Notice: Subject to any disclaimer, the term of this patent is extended or adjusted under 35 U.S.C. 154(b) by 4 days.

(21) Appl. No.: 15/782,671

(22) Filed: Oct. 12, 2017

(65) Prior Publication Data
US 2019/0070235 A1   Mar. 7, 2019

(30) Foreign Application Priority Data

Sep. 4, 2017   (TW) .............................. 106130184 A

(51) Int. Cl.
*A61K 36/07* (2006.01)
*A61K 36/484* (2006.01)
*A61K 36/88* (2006.01)

(52) U.S. Cl.
CPC ............ *A61K 36/07* (2013.01); *A61K 36/484* (2013.01); *A61K 36/88* (2013.01)

(58) Field of Classification Search
None
See application file for complete search history.

(56) References Cited

U.S. PATENT DOCUMENTS 9,272,010 B2 *  3/2016  Chen ..................... A61K 36/07

OTHER PUBLICATIONS

Adianti et al. (Microbiology and Immunology, 2014, vol. 58, p. 180-187).*
Chen (Zhong Xi, 1990, vol. 10 Abstract).*
Yue et al. (Chinese Medicine, 2013, vol. 8, p. 1-7).*
Miranda-Pettersen et al, "The fatigue impact scale for daily use in patients with hepatitis B virus and hepatitis C virus chronic infections", Annals of Hepatology, May-Jun. 2015, vol. 14, p. 310-316.
Patidar et al., "Tired of Hepatitis B?", Dig Dis Sci, 2016, vol. 61, p. 953-954.

* cited by examiner

*Primary Examiner* — Agnieszka Boesen
(74) *Attorney, Agent, or Firm* — WPAT, PC

(57) ABSTRACT

A method for treating hepatitis B comprises administering a herbal extract to a subject in need thereof to suppress survival of hepatitis B virus. The herbal extract is manufactured by extracting a herbal composition by a 70-95% aqueous ethanol solution at 40-50° C. The herbal composition comprises 40 wt % of a fruit body sample of *Antrodia cinnamomea*, 40 wt % of a sample of *Polygonatum sibiricum* and 20 wt % of a sample of *Glycyrrhiza uralensis*.

4 Claims, 2 Drawing Sheets

METHOD FOR TREATING HEPATITIS B

CROSS REFERENCE TO RELATED APPLICATIONS

The application claims the benefit of Taiwan application serial No. 106130184, filed on Sep. 4, 2017, and the entire contents of which are incorporated herein by reference.

BACKGROUND OF THE INVENTION

1. Field of the Invention

The present invention relates to a method for treating hepatitis B and, more particularly, to a method for treating hepatitis B using a herbal extract.

2. Description of the Related Art

Hepatitis B is a common disease in Taiwan. About 15% of adults are hepatitis B virus carriers. The derivative diseases caused by hepatitis B virus, such as chronic liver illnesses, cirrhosis, liver cancer (hepatocellular carcinoma), are the top on the list of general causes of death in Taiwan.

*Antrodia cinnamomea* is fungus indigenous to Taiwan and grows on decayed *Cinnamomum kanehirai*. Antroquinonol, an active substance rich in *Antrodia cinnamomea*, has an activity for suppressing survival of hepatitis B virus-carrying cell line.

*Antrodia cinnamomea* belongs to herbs with cold property and shows effects on removing free radicals and mitigating inflammation. However, a long-term application of *Antrodia cinnamomea* may excessively remove free radicals, resulting in a cold constitution with reduced immunity. Thus, it is necessary to develop a novel method for treating hepatitis B.

SUMMARY OF THE INVENTION

It is therefore the objective of the present invention to provide a method for treating hepatitis B by using a herbal extract which is rich in active substances against hepatitis B virus.

One embodiment of the present invention discloses a method for treating hepatitis B. The method comprises administering a herbal extract to a subject in need thereof to suppress survival of hepatitis B virus, wherein the herbal extract is manufactured by extracting a herbal composition by a 70-95% aqueous ethanol solution at 40-50° C. The herbal composition comprises 40 wt % of a fruit body sample of *Antrodia cinnamomea*, 40 wt % of a sample of *Polygonatum sibiricum* and 20 wt % of a sample of *Glycyrrhiza uralensis*. Preferably, the herbal extract is orally administered to the subject in need thereof in a dosage of 200 mg/per kilogram of body weight per day for 7 days.

Accordingly, with the active substances extracted from the herbal composition including the fruit body sample of *Antrodia cinnamomea*, the herbal extract according to the present invention shows abilities of suppressing survival of hepatitis B virus and of helping the clearance of hepatitis B virus. Moreover, a long-term application of the herbal extract of the invention will not result in reduced immunity, which is a side effect of the long-term application of *Antrodia cinnamomea*.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

DETAILED DESCRIPTION OF THE INVENTION

Figure 1:
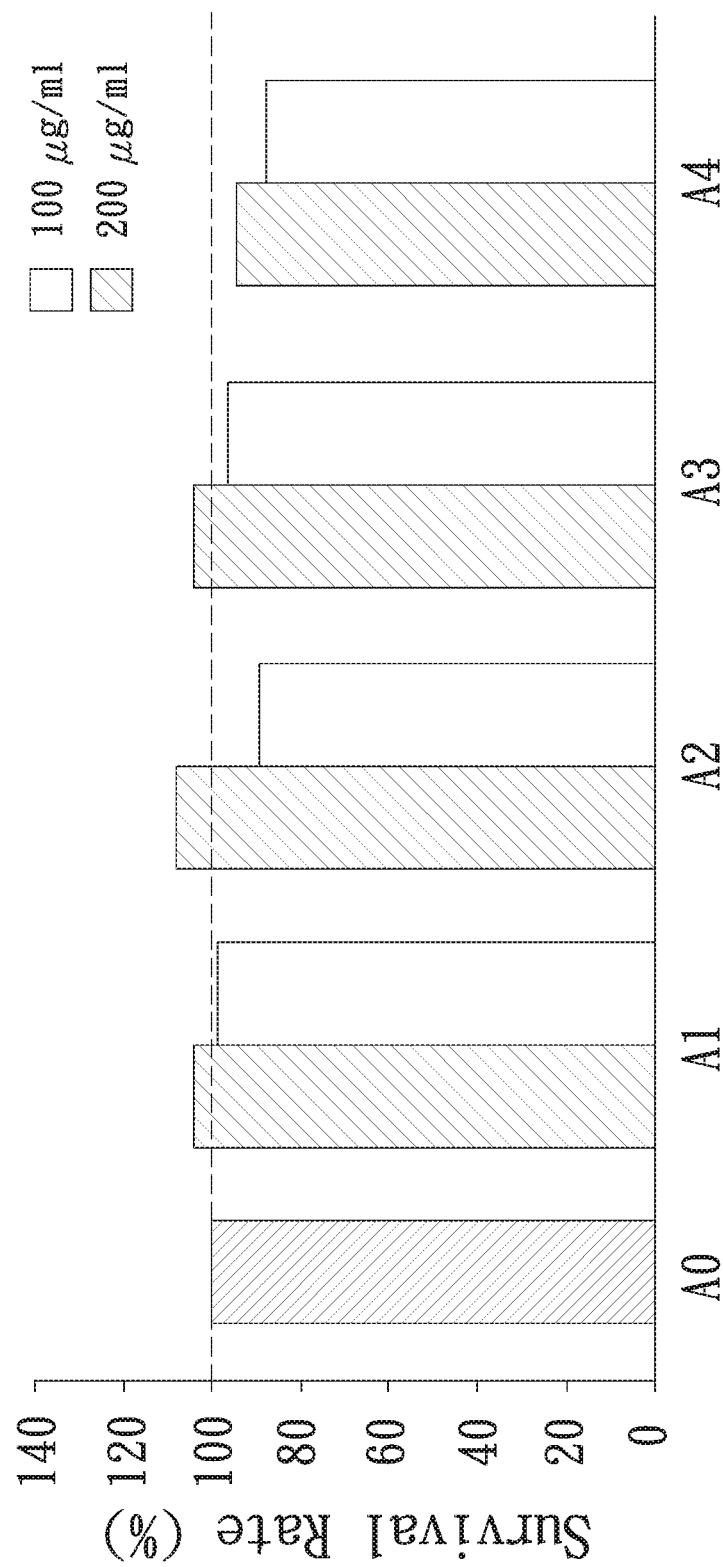
FIG. 1 is a bar chart illustrating the relative survival rate of the Hep3B cell in the presence of a herbal extract according to the present invention.

A herbal extract according to the present invention can suppress survival of hepatitis B virus and can help the clearance of hepatitis B virus in bodies. Therefore, the herbal extract can be applied to treat hepatitis B. The herbal extract can be used individually, or in combination with pharmaceutical acceptable vehicles, excipients, salts or other nutrients, being in a composite. In addition, the herbal extract can be further manufactured into any oral type that is easy to take, such as pastil, capsule, powder, pill, solution, or fermented products. Yet, the herbal extract can be combined with other food products or drinks, being manufactured into a more convenient type for taking.

The herbal extract according to the present invention can be administered to a subject in need thereof. As an example, the herbal extract can be administered in a dosage of 200 mg/per kilogram of body weight per day for 7 days. Therefore, the active substances of the herbal extract can suppress survival of hepatitis B virus and help the clearance of hepatitis B virus.

The herbal extract can be preferably obtained by a method including the following steps: providing a herbal composition; extracting the herbal composition by an aqueous ethanol solution (about 70-95% by weight) as an extractant to obtain a rough extract; and concentrating the rough extract to obtain the herbal extract.

Specifically, the herbal composition can include 40 wt % of a sample of *Antrodia cinnamomea*, 40 wt % of a sample of *Polygonatum sibiricum* and 20 wt % of a sample of *Glycyrrhiza uralensis*. It is worthy to note that a fruit body sample of *Antrodia cinnamomea* is preferably chosen as the sample of *Antrodia cinnamomea* because the fruit body sample of *Antrodia cinnamomea* is abundant in triterpenes with the benefit of anti-inflammation. Moreover, a root sample of *Polygonatum sibiricum* and a root sample of *Glycyrrhiza uralensis* are respectively selected as the sample of *Polygonatum sibiricum* and the sample of *Glycyrrhiza uralensis*. Both the root sample of *Polygonatum sibiricum* and the root sample of *Glycyrrhiza uralensis* are easily obtained and thus the manufacture cost of the herbal extract can be decreased.

The worker can mill the sample of *Antrodia cinnamomea*, the sample of *Polygonatum sibiricum* and the sample of *Glycyrrhiza uralensis* in advance as well. With such performance, the contacting surface area of the sample of *Antrodia cinnamomea*, the sample of *Polygonatum sibiricum* and the sample of *Glycyrrhiza uralensis* with the aqueous ethanol solution is increased. Therefore, the efficiency of the extraction is also increased.

In an example, the worker can mix the herbal composition with the aqueous ethanol solution in a weight to volume ratio of 1:10. For example, 100 grams of the herbal composition is mixed with 1 liter of the aqueous ethanol solution. The herbal composition is then extracted at 40-50° C. for 8 hours.

The extraction process can be repeated several times, assuring the active substances of the herbal composition can be completely dissolved in the extractant, which can be appreciated by a person having ordinary skill in the art.

Furthermore, the rough extract can be further concentrated by concentration under reduced pressure and lyophilization to obtain the herbal extract. The active substances of the herbal extract are further concentrated. The preferable efficacy for treating hepatitis B will be achieved by only a limited amount of the herbal extract.

To validate the herbal extract according to the present invention can be used to help clearance of hepatitis B virus, the rough extract from 100 grams of the herbal composition is concentrated under reduced pressure and lyophilization to obtain 12 grams of the herbal extract in a powder form. The herbal extract (1 gram) is then dissolved in DMSO (dimethylsulfoxide, 500 mL) for the following trials.

Trial (A).

The Hep3B cells are used in the trial (A). An extract of *Polygonatum sibiricum* (group A1, obtained from extracting the root sample of *Polygonatum sibiricum* by the 95% aqueous ethanol solution), an extract of *Glycyrrhiza uralensis* (group A2, obtained from extracting the root sample of *Glycyrrhiza uralensis* by the 95% aqueous ethanol solution), an extract of *Antrodia cinnamomea* (group A3, obtained from extracting the fruit body sample of *Antrodia cinnamomea* by the 95% aqueous ethanol solution) and the herbal extract according to the present invention (group A4) are used to treat the Hep3B cells for 24 hours, respectively. The survival rates of the treated Hep3B cells are calculated and the survival rate of the Hep3B cells treated by DMSO (group A0) is regarded as 100%.

Referring to FIG. 1, the survival rates of the Hep3B cells of groups A1-A4 treated by the extract of *Polygonatum sibiricum*, the extract of *Glycyrrhiza uralensis*, the extract of *Antrodia cinnamomea* and the herbal extract according to the present invention, respectively, show no significant difference from the survival rate of the Hep3B cells of group A0, indicating the herbal extract according to the present invention shows no significant cytotoxicity to the Hep3B cells.

Trial (B).

The Hep3B cells are also used in the trial (B). The extract of *Polygonatum sibiricum* (group B1), the extract of *Glycyrrhiza uralensis* (group B2), the extract of *Antrodia cinnamomea* (group B3) and the herbal extract according to the present invention (group B4) are used to treat the Hep3B cells for 24 hours, respectively. The hepatitis B surface antigen (HBsAg) contents in the culture medium culturing the Hep3B cells of groups B1-B4 are then measured. The HBsAg content in the culture medium culturing the Hep3B cells treated by DMSO (group B0) is regarded as 100%.

Figure 2:
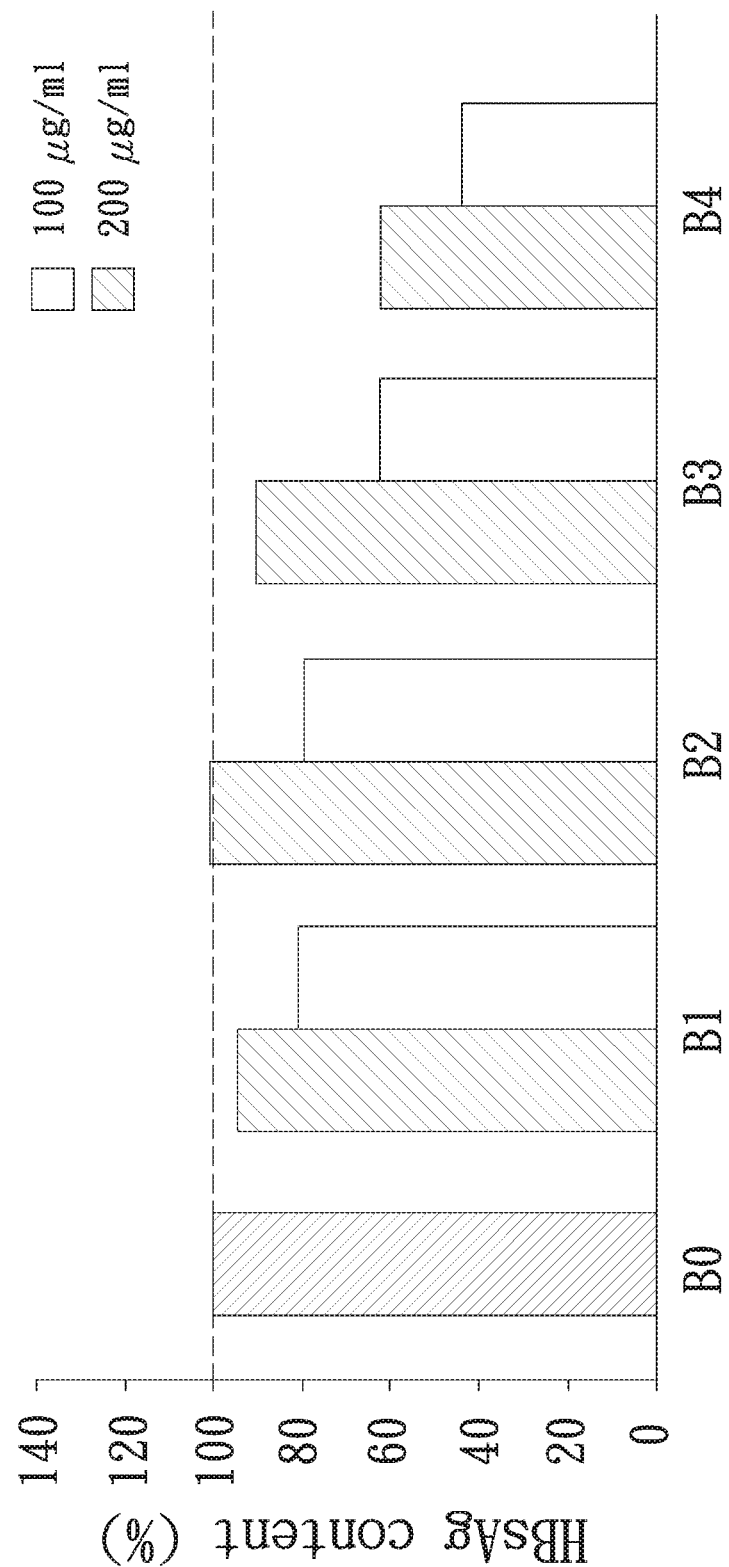
FIG. 2 is a bar chart illustrating the relative hepatitis B surface antigen (HBsAg) content in the culture medium in the presence of a herbal extract according to the present invention.

With reference to FIG. 2, the HBsAg content in the culture medium culturing the Hep3B cells treated by the herbal extract according to the present invention is the lowest, indicating the herbal extract according to the present invention can suppress survival of hepatitis B virus to help the clearance of hepatitis B virus.

Accordingly, with the active substances extracted from the herbal composition including the fruit body sample of *Antrodia cinnamomea*, the herbal extract according to the present invention shows abilities of suppressing survival of hepatitis B virus and of helping the clearance of hepatitis B virus. Moreover, a long-term application of the herbal extract of the invention will not result in reduced immunity, which is a side effect of the long-term application of *Antrodia cinnamomea*.

In addition, with the active substances extracted from the herbal composition including the fruit body sample of *Antrodia cinnamomea*, the herbal extract according to the present invention can be used to effectively decrease the risk of infection of hepatitis B virus. Therefore, the herbal extract can also be used to prevent from the diverse of the derivative diseases, such as chronic liver illnesses, cirrhosis, prolonged prothrombin time, and liver cancer (hepatocellular carcinoma).

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for treating hepatitis B, comprising:
  administering a herbal extract to a subject in need thereof to suppress survival of hepatitis B virus, wherein the herbal extract is manufactured by extracting a herbal composition by a 70-95% aqueous ethanol solution at 40-50° C., wherein the herbal composition comprises 40 wt % of a fruit body sample of *Antrodia cinnamomea*, 40 wt % of a sample of *Polygonatum sibiricum* and 20 wt % of a sample of *Glycyrrhiza uralensis*.

2. The method for treating hepatitis B as claimed in claim 1, wherein the herbal extract is orally administered to the subject in need thereof.

3. The method for treating hepatitis B as claimed in claim 2, wherein the herbal extract is administered to the subject in need thereof in a dosage of 200 mg/per kilogram of body weight per day.

4. The method for treating hepatitis B as claimed in claim 3, wherein the herbal extract is administered to the subject in need thereof for 7 days.

* * * * *